(12) United States Patent
Heer et al.

(10) Patent No.: US 8,793,084 B2
(45) Date of Patent: Jul. 29, 2014

(54) METHOD FOR WIRELESS DATA TRANSMISSION BETWEEN A MEASUREMENT MODULE AND A TRANSMISSION UNIT

(75) Inventors: Rudolf Heer, Vienna (AT); Hubert Brueckl, Wiener Neudorf (AT); Hans Kroath, Baden (AT); Juergen Wissenwasser, Vienna (AT)

(73) Assignee: AIT Austrian Institute of Technology GmbH, Vienna (AT)

( * ) Notice: Subject to any disclaimer, the term of this patent is extended or adjusted under 35 U.S.C. 154(b) by 696 days.

(21) Appl. No.: 12/992,640

(22) PCT Filed: May 14, 2009

(86) PCT No.: PCT/AT2009/000198
§ 371 (c)(1),
(2), (4) Date: Feb. 8, 2011

(87) PCT Pub. No.: WO2009/137858
PCT Pub. Date: Nov. 19, 2009

(65) Prior Publication Data
US 2011/0125428 A1  May 26, 2011

(30) Foreign Application Priority Data

May 14, 2008  (AT) .................................. A 770/2008

(51) Int. Cl.
*G01R 15/00* (2006.01)
*G01R 21/00* (2006.01)
*G01R 21/06* (2006.01)
*G01R 21/133* (2006.01)

(52) U.S. Cl.
CPC .................................. *G01R 21/1331* (2013.01)
USPC ............................................. 702/57; 702/62

(58) Field of Classification Search
CPC ........................ G01R 19/2506; G01R 21/1331
USPC ..................................................... 702/57, 62
See application file for complete search history.

(56) References Cited

U.S. PATENT DOCUMENTS

| | | | |
|---|---|---|---|
| 5,041,826 A * | 8/1991 | Milheiser | 340/10.42 |
| 5,053,774 A | 10/1991 | Schuermann et al. | |
| 5,355,137 A * | 10/1994 | Schurmann | 342/42 |
| 5,597,534 A | 1/1997 | Kaiser | |
| 6,411,212 B1 * | 6/2002 | Hecht et al. | 340/572.1 |
| 2003/0085707 A1 * | 5/2003 | Minerbo et al. | 324/343 |
| 2003/0114769 A1 | 6/2003 | Loeb et al. | |
| 2005/0261562 A1 | 11/2005 | Zhou et al. | |
| 2008/0278331 A1 * | 11/2008 | Hayter et al. | 340/573.1 |
| 2011/0256893 A1 * | 10/2011 | Athley et al. | 455/500 |

\* cited by examiner

*Primary Examiner* — Michael Nghiem
(74) *Attorney, Agent, or Firm* — Laurence A. Greenberg; Werner H. Stemer; Ralph E. Locher

(57) ABSTRACT

A method records and transmits data between a transmission unit that has a first antenna and a measurement module which has a sensor for recording measured variables and converts the measured variables into electric signals. Data is bi-directionally transmitted between the measurement module and the transmission unit located within the near field of the measurement module by use of a second antenna that is arranged on the measurement module. The electromagnetic energy of the signal that is applied to the second antenna is transformed and temporarily stored by a reception unit which is arranged downstream of the second antenna. The first antenna of the transmission unit is put in an inactive state at least during the time the measured variables are sensed by the measurement module or the sensors.

3 Claims, 4 Drawing Sheets

METHOD FOR WIRELESS DATA TRANSMISSION BETWEEN A MEASUREMENT MODULE AND A TRANSMISSION UNIT

BACKGROUND OF THE INVENTION

1. Field of the Invention

The invention relates to a method and a configuration for recording and transmitting data between a transmission unit having an antenna and a measurement module having at least one sensor for recording measured variables, including biological variables.

Methods and arrangements according to the invention are used in particular for on-line monitoring and detecting measured variables or biologic reactions, particularly the electric properties of cell cultures.

Typically, for determining biological properties of a sample, the impedance of this sample is detected at one or more predetermined frequencies. By a plurality of impedances measured at different frequencies, one can draw conclusions on the biologic properties of the sample. To make measurement simple and cost effective, one can provide that the measurement modules, wherein the biological samples are, and the transmission units, which transfer the measured data to a central data processing unit, are realised as separate units. For simple transmission between the transmission unit and the measurement module, wireless data transmission methods can be employed, particularly RFID transmission methods. In a preferred manner, one can provide that the measurement modules are realised as passive RFID components, i.e. that the energy supply of the measurement modules is effected over an electromagnetic signal emanating from the transmission unit, an intermediate storage of energy being effected within the measurement module.

An essential problem of the prior art consists in that the measurement of the impedance of the biologic samples as well as the transmission of measured data are realised by means of quickly changing electromagnetic fields. For this reason, interferences may occur during recording of the measured data, which are caused by the transmission of measured data being already measured before, or by the simultaneous transmission of energy.

2. Brief Summary of the Invention

The invention has the object to solve the above-mentioned problems and to provide a method and a measuring arrangement which overcome said problems.

With the foregoing and other objects in view there is provided, in accordance with the invention a method for recording and transmitting data between a transmission unit having a first antenna and a measurement module having at least one sensor for recording measured variables, including biological variables, and transforms the measured variables into electrical signals and a measuring amplifier coupled to the sensor. The method includes performing a bidirectional transmission of the data between the measurement module and the transmission unit, disposed in a near range of the measurement module, using a second antenna situated on the measurement module. Via a reception unit coupled to the second antenna, electromagnetic energy of a signal present at the second antenna is transformed. The electromagnetic energy is immediately stored and made available in a form of a voltage level at an output. The stored electromagnetic energy is delivered to the sensor and the measuring amplifier as a current supply. Components of the measuring module are controlled via a central data processing unit of the measurement module, while being supplied with the electromagnetic energy stored in the reception unit. The central data processing unit further processes the measured signals of the sensor and communicates with the transmission unit. The first antenna of the transmission unit is set to be inactive for a time period of a determination of the measured variables by the sensor. The setting to inactive is effected at an instigation of the measurement module, which signals to the transmission unit that a storing unit, connected to the reception unit, is fully charged and further signals from the transmission unit should be stopped in a sense of a disturbance-free measurement.

In addition the invention relates to a configuration containing a measurement module, and a transmission unit having a first antenna and an antenna driver for controlling the first antenna. The transmission unit transmits data by use of the first antenna to the measurement module and processes the data received from the measurement module by use of the first antenna. The measurement module contains at least one sensor for recording measured variables, a measuring amplifier coupled to the sensor, a second antenna for bidirectional transmission of the data between the measurement module and the transmission unit disposed in a near range of the measurement module, and a reception unit having an output and coupled to the second antenna. The reception unit transforms and intermediately stores electromagnetic energy of a signal present at the second antenna and puts the electromagnetic energy available in a form of a voltage level existing at the output, and delivers the stored electromagnetic energy to the sensor and to the measuring amplifier as a current supply. A central data processing unit supplied by the electromagnetic energy stored in the reception unit, controls components of the measurement module. The central data processing unit further processes measured signals of the sensor and communicates with the transmission unit. The antenna driver has a circuit for timely limited stopping or for electrical inactivation of the first antenna when receiving a stop signal emitted by the second antenna.

The method also includes the following steps. Setting the first antenna to be active for transmitting the electromagnetic energy to the reception unit, transmitting the electromagnetic energy between the first antenna and the second antenna, and storing the electromagnetic energy in the measurement module. After transmission of a predetermined amount of the electromagnetic energy, transmitting or transferring a control pulse, generated by the measurement module, to the transmission unit, by which the first antenna is set inactive for a predetermined time period. During the predetermined time period, effecting the measurement of the measured variables to be determined. After the end of the predetermined time period, setting the antenna of the transmission unit to be active again. After an end of the measurement, transmitting measured data in coded form from the measurement module to the transmission unit. The method may include a step of after an end of the predetermined time period transmitting the measured data in coded form from the measurement module to the transmission unit.

An essential advantage of the method according to the invention and of the arrangement according to the invention consists in that during detecting the measured variables by the measurement module, no interferences occur between the electromagnetic signal required for measurement and the signal for the transmission of data or energy. Thus, accuracy and the signal-to-noise ratio (SNR) of the measurement is greatly improved, wherein particularly the quality of the impedance measurement is particularly greatly improved in those frequency bands or their harmonic waves or sub-harmonic waves, which coincide with the frequency band that is employed for data transmission. Thus, the invention avoids interferences between in the near field between antennas used for transmission of data and energy, and the components provided for determining the measured variables on the measurement module.

In accordance with an added mode of the invention, the sensors are used to determine an impedance of a sample situated in the measurement module at a predetermined number of frequencies and therefore a particularly precise assertion can be made on the character of biological samples.

With the features of the invention, a particularly simple course of procedure is warranted, which comprises a high failure tolerance and increases the stability of the measurement procedure.

An arrangement where the transmission unit has a plurality of first antennas and a plurality of bidirectional antenna drivers, and each of the bidirectional antenna drivers is connected to each of the first antennas and the measurement module is one of a plurality of measurement modules with each of the measurement modules having a separate second antenna allows integration of a plurality of measurement modules on a transmission unit in common in a simple manner.

DESCRIPTION OF THE INVENTION

Figure 1:
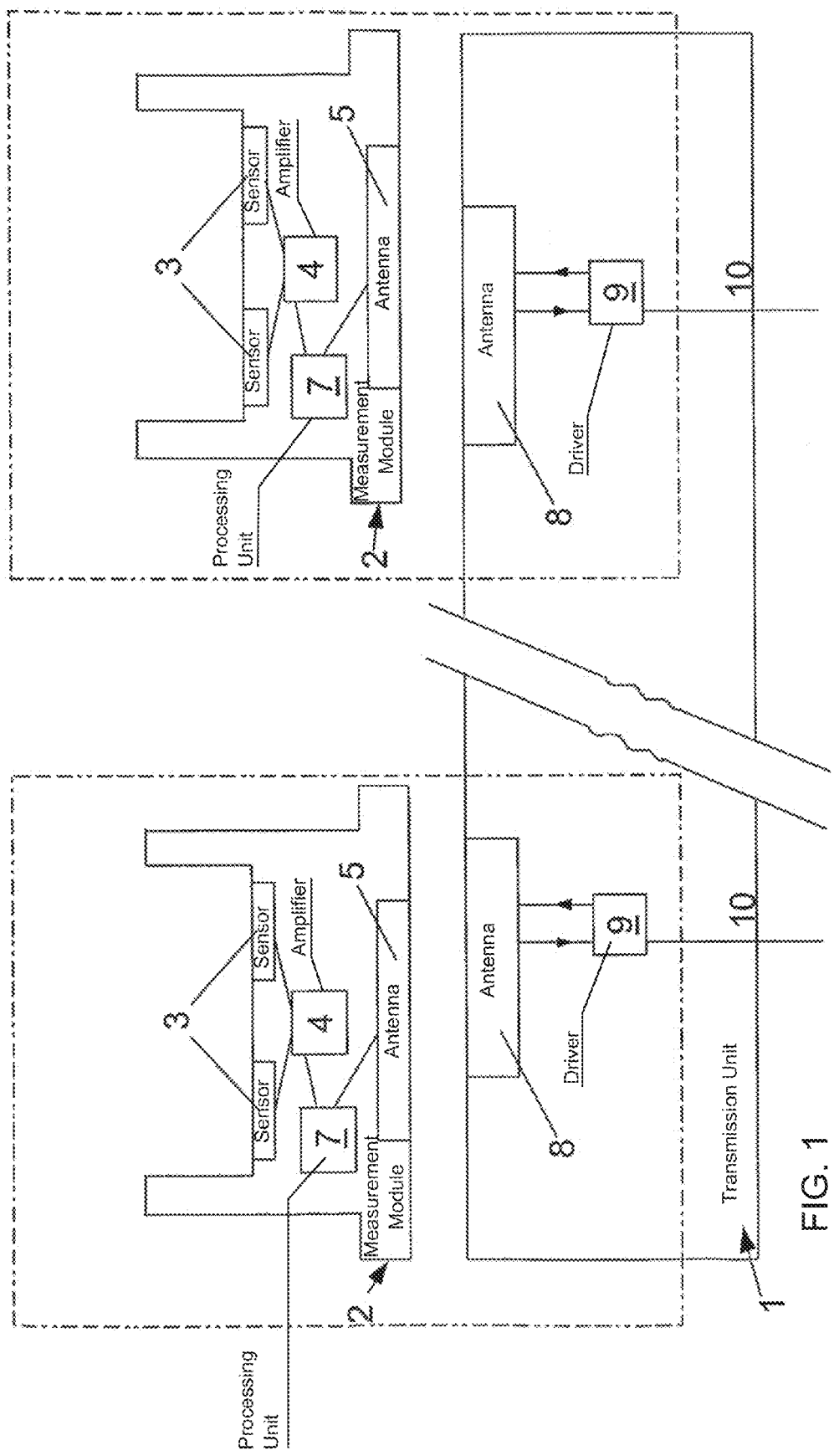
FIG. 1 shows a measuring set-up, according to the invention, comprising a transmission unit as well as two measurement modules.

FIG. 1 shows a transmission unit 1 as well as two measurement modules 2 being in radio link with this transmission unit 1. This transmission unit 1 comprises therein a plurality of first antennas 8, wherein a first antenna 8 is assigned to each measurement module 2, and wherein this first antenna is situated in the near range of the measurement module 2. An antenna driver 9 is assigned to each first antenna 8 and enables a bidirectional communication with the antenna 8. Furthermore, a further output for a supply line 10 or a data line 10 in common is provided on the antenna driver 9 for a plurality of first antennas 8 or the respective associated antenna drivers 9 situated in the transmission unit 1.

Above the first antennas 8, measurement modules 2 are represented comprising a second antenna 5, which is in electromagnetic cooperative connection with the respective associated first antenna 8. Each one of the first antennas 8 is arranged immediately below the associated second antenna 5, wherein a distance of some millimeters may exist between the two antennas 5, 8 associated to each other. Each measurement module 2 comprises a sample receptacle, into which biological test material may be filled. The sensors 3 are typically arranged at the inner edge of the respective sample receptacle.

Figure 2:
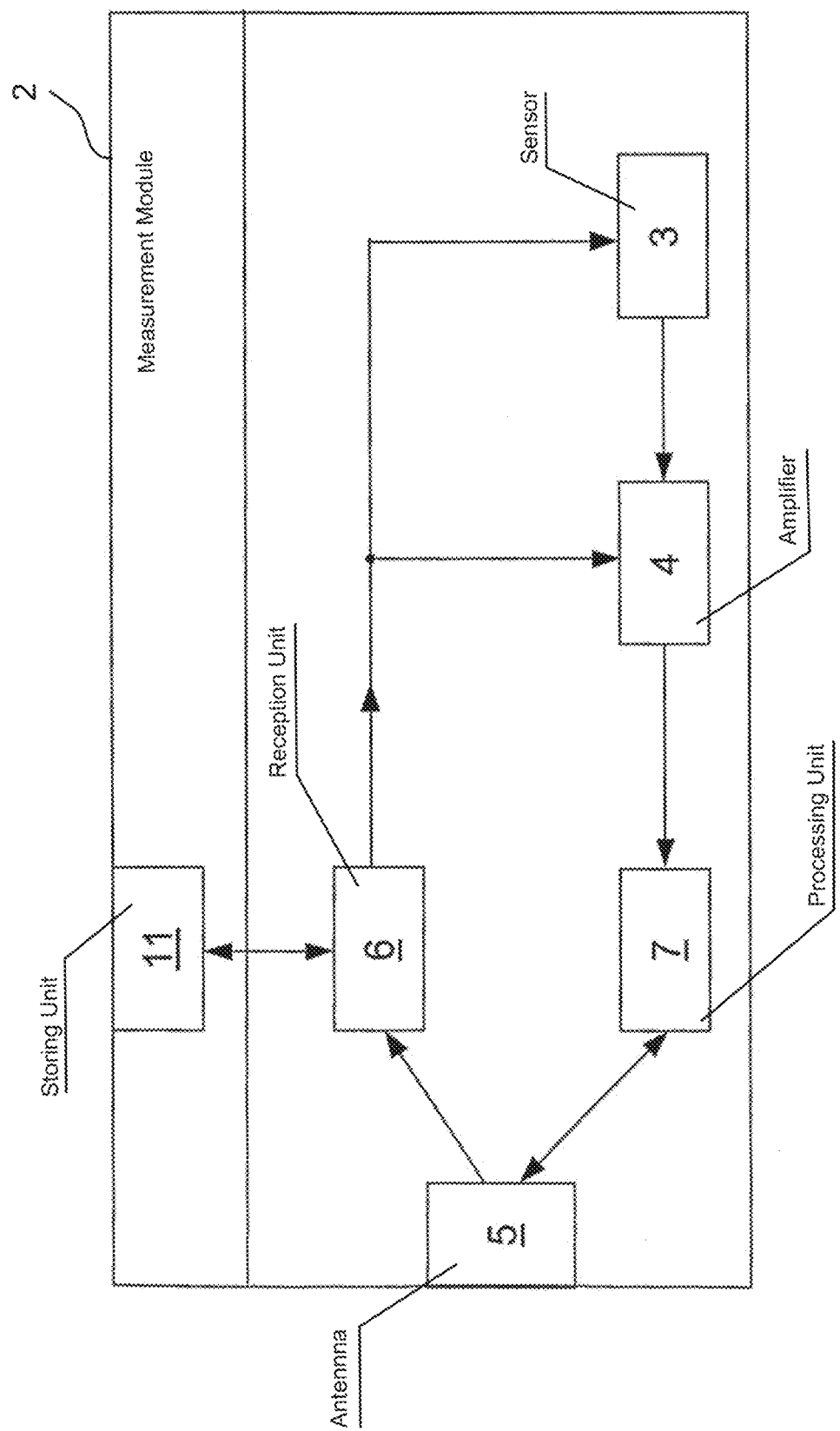
FIG. 2 shows schematically the design of a measurement module.

As schematically illustrated in FIG. 2, each one of the measurement modules 2 comprises one or more sensors for recording a plurality of physical measured variables as well as for the conversion thereof into electrical signals. One or more respective measuring amplifier(s) 4 are each postponed to these sensors for amplification and, optionally, for analogue to digital conversion of the signal amplitude or the course of signal. Furthermore, a central data processing unit 7 is provided within the measurement module 2, which is connected both to a sensor 3, optionally to the measuring amplifier 4, and to the respective second antenna 5. In this central data processing unit 7, particularly in a micro-controller, the measured data determined and, optionally digitised, are processed, memorised and, optionally fed for preparing analyses. The central data processing unit 7 is connected to the second antenna 5, wherein a communication control unit is interposed between the central data processing unit 7 and the second antenna 5, which enables communication between the central data processing unit 7 and a calculating node connected to the transmission unit 1. Such a communication control unit can also exist as an integral component of the central data processing unit 7.

Furthermore, a reception unit 6 is connected to the second antenna 5, which transforms the electromagnetic energy of the signal present at the second antenna 5, memorises it intermediately and puts it at disposal in the form of a voltage level present at its output. This reception unit 6 is connected to a buffer store for electrical energy which allows to continue further with operation of the central data processing unit 7, of the sensors 3 and of the measuring amplifiers 4, even if, at a given moment, no energy is transmitted from the transmission unit 1 to the respective measurement module 2. Thus, there is the possibility, that a measurement can be continued, even if no immediate energy transmission is effected from the first antenna 8 to the second antenna 5. The stored energy is put at disposal at the output of the reception unit 6 in form of a voltage level, wherein the stored energy is delivered for current supply to the sensors, the measuring amplifier and to the central data processing unit 7. The lines for voltage supply of the central data processing unit, of the measuring amplifiers as well of the sensors are not shown in FIG. 1.

Figure 4:
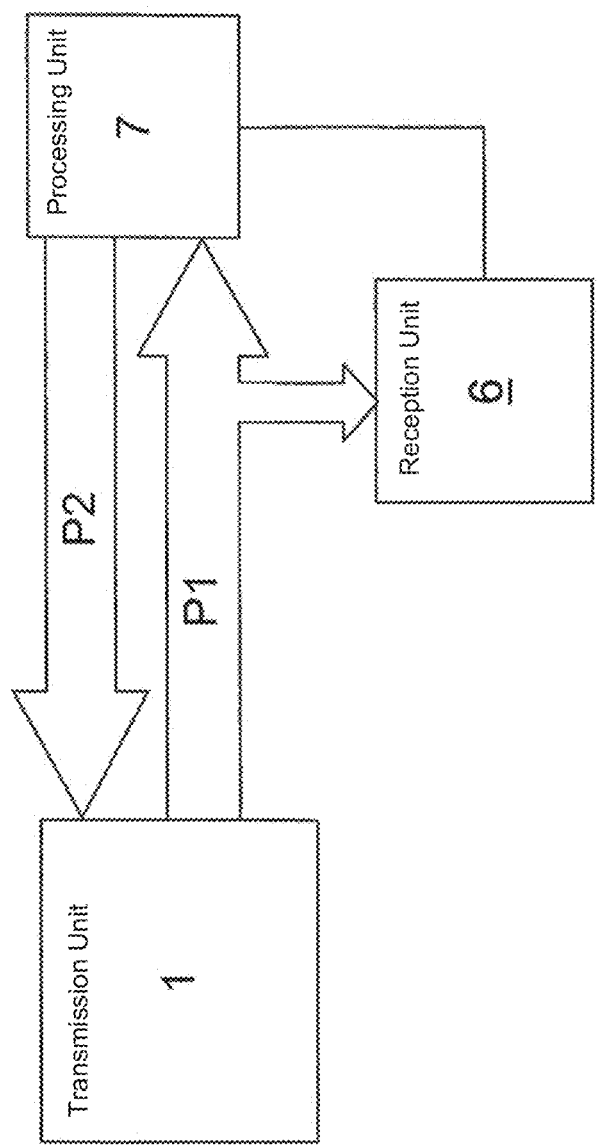
FIG. 4 shows schematically the transmission of energy and information in the form of electromagnetic waves.

In FIG. 4, the energy and data transmission between the transmission unit 1 and a measurement module 2 are illustrated. Electromagnetic energy P1 is transmitted from the transmission unit 1 to the measurement module 2. Apart from dissipation losses, the electromagnetic energy P1 transmitted by the transmission unit 1 is received in the measurement module by the second antenna 5, and the energy received is divided between the reception unit 6 and the data processing unit 7. Storing of the transmitted energy is effected in the storing unit 11 connected to the reception unit 6. This storing unit 11 comprises a voltage regulator, which enables supply of constant voltage to the measurement module 2. The data processing unit 7 or the communication controller put in series before the data processing unit 7 determines control information from the electromagnetic data signals, which are provided for controlling the measurement module 2. By means of this signal, the measurement module 2 and the central data processing unit 7 can be controlled by the transmission unit 1. Excess of energy P1 is fed to the reception unit 6, which transforms the energy stored in the signal also into electrical energy and puts it at disposal in the form of a voltage level existing at its output. Thus, that energy is at disposal for measurement by means of the sensors 3 as well as for transmission of data from the second antenna 5 to the first antenna 8, which is stored in the reception unit 6. Such a configuration of the measurement module 2, which manages without a permanent energy source, is called a passive one in the following. Its only one of the two communication participants which needs an external energy source for maintaining the communication, whereas the respective other communication participant, i.e. the measurement module 2, determines its energy from the data signal of its communication partner.

To carry out the method according to the invention, one proceeds as follows: The transmission unit 1 is set active and transmits an electromagnetic signal to the measurement module 2 associated to it. In doing so, energy in the form of an electromagnetic signal is transmitted from the transmission unit 1 via the first antenna 8 and the second antenna 5 to the reception unit 6, by which the voltage level existing at the output of the reception unit 6 strives towards a maximum value. As soon as this maximum value is attained, there is sufficient energy for carrying out a measuring procedure. The first antenna 8 of the transmission unit 1 is set inactive, and measurement of the impedance of the sample by means of the two sensors 3 is started. Here is noteworthy that the measurement can no longer be disturbed by the electromagnetic signal emitted by the first antenna 8. Thus, the disturbance generated by the interference between the measuring signal emitted by the sensor 3 and the data signal emitted by the first antenna 8 can completely be eliminated. By this, also noise, which concerns to a vast extend the measuring values determined by the sensors 3, is eliminated to a high degree.

A particular embodiment of the method according to the invention concerns the control of operating sequence. It is essential for carrying out a measurement, that as much energy exists before beginning a measuring procedure that the measurement can completely be performed. Otherwise, no more energy would be at disposal during performance of the measurement, by which it could be that the measured data already stored are lost.

Figure 3:
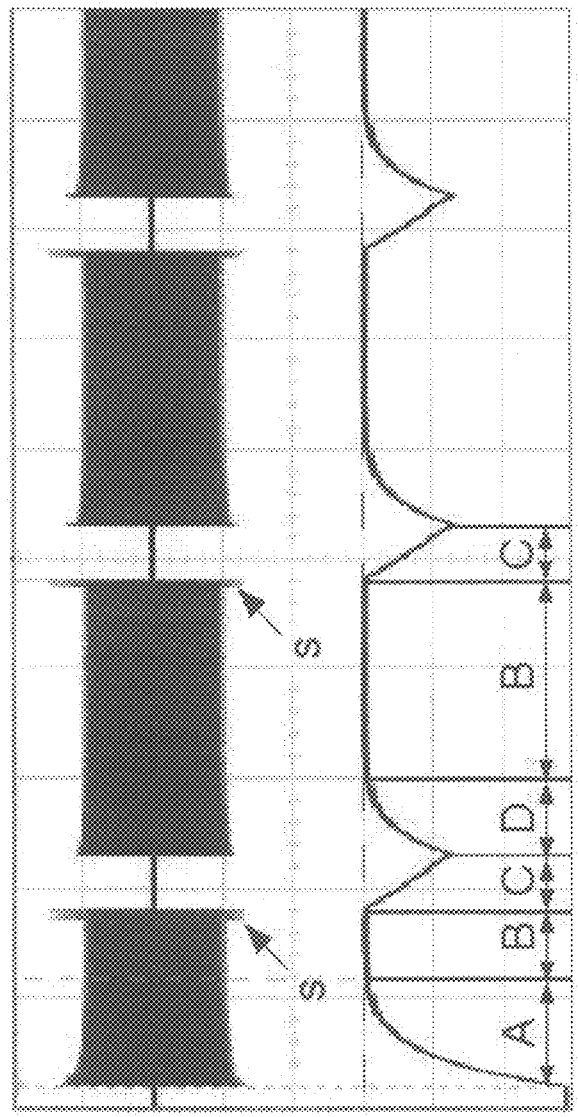
FIG. 3 represents a timing diagram, which illustrates the temporarily stored supply voltage within the measurement module as well as the signals transmitted by the respective transmission antennas of the transmission unit and the measurement modules in the course of time.

The upper graph of FIG. 3 represents the course of time of the data signal transmitted between the first antenna 8 and the second antenna 5. The lower graph of FIG. 3 represents the electrical energy stored in the reception unit 6. At the beginning of the method, no energy is still stored in the reception unit 6. Within a time period A of about 200 ms, the signal transmitted from the transmission unit 1 by means of the first antenna 8 and the second antenna 5 to the measurement module 2 is used to charge the energy store of the reception unit 6. During a data transmission phase B, the energy stored in the measurement module 2 strives towards a predetermined value. Moreover, data can be exchanged between the measurement module 2 and the transmission unit 1 during this data transmission phase B. At the end of the data transmission phase B, the measurement module 2 transmits a stopping signal S via its second antenna 5, which causes the first antenna 8 of the transmission unit 1 to be set inactive. This inactive setting is done at the instigation of the measurement module 2, which signals to the transmission unit 1, that the storing unit 11 connected to the reception unit 6 is fully charged and further signals from the transmission unit 1, in the sense of a disturbance-free measurement, should be stopped. The first antenna 8 of the transmission unit 1 is set inactive for a predetermined time period of about 100 ms, and during this time, the measuring procedure is effected in the measurement module 2. As represented in the lower graph, the energy stored in the reception unit 6 decreases during a subsequent data determining phase C. After a predetermined time has lapsed, the first antenna 8 of the transmission unit 1 is set active again, by which the reception unit 6 is again charged anew during a subsequent charging phase D. After the end of the charging phase D, data may be transmitted from the measurement module 2 to the transmission unit 1. In doing this, the energy stored in the measurement module 2 remains approximately constant, because despite of the electrical activity in the measurement module 2, energy is constantly supplied via the first antenna 8 to the measurement module 2. After the end of the data transmission B, the measurement module 2 gives a stopping pulse S, and the measuring procedure can be carried out anew. Typically, such a procedure is repeated ten or twenty times as far as all data to be determined have been received by the sensors 3 and have been transmitted to the transmission unit 1.

An advantageous embodiment of the arrangement according to the invention will be obtained, if a first antenna 8 is assigned to each one of the measurement modules 2, and a separate antenna driver is assigned to each first antenna 8. After reduction of the data emergence in the antenna drivers 9, a data line 10 with a small data emergence is at disposal. These data lines 10 may, optionally, be connected to become a bus, and are led to a calculation node in common.

The invention claimed is:

1. A method for recording and transmitting data between a transmission unit having a first antenna and a measurement module having at least one sensor for measuring variables, including biological variables, and transforms the measured variables into electrical signals and a measuring amplifier coupled to the sensor, which comprises the steps of:

performing a bidirectional transmission of the data between the measurement module and the transmission unit, disposed in a near range of the measurement module, using a second antenna situated on the measurement module;

transforming, via a reception unit coupled to the second antenna, electromagnetic energy of a signal present at the second antenna to electrical energy;

intermediately storing the electrical energy, outputting the stored electrical energy in a form of a voltage level at an output of the reception unit, and delivering the stored electrical energy as a current to the sensor and the measuring amplifier;

controlling components of the measuring module via a central data processing unit of the measurement module, while being supplied with the electrical energy stored in the reception unit, the central data processing unit further processing the measured variables of the sensor and communicating with the transmission unit;

setting the first antenna of the transmission unit to be inactive for a time period of a determination of the measured variables by the sensor; and effecting the setting to inactive at an instigation of the measurement module, which signals to the transmission unit that a storing unit, connected to the reception unit, is fully charged and further signals from the transmission unit should be stopped; and which further comprises:

a) setting the first antenna to be active for transmitting the electromagnetic energy to the reception unit, transmitting the electromagnetic energy between the first antenna and the second antenna, and storing the electrical energy in the measurement module;

b) after transmission of a predetermined amount of the electromagnetic energy, transmitting or transferring a control pulse, generated by the measurement module, to the transmission unit, by which the first antenna is set inactive for a predetermined time period;

c) during the predetermined time period, effecting a measurement of the measured variables to be determined;

d) after the end of the predetermined time period, setting the first antenna of the transmission unit to be active again; and e) after an end of the measurement of the measured variables, transmitting the measured variables in coded form from the measurement module to the transmission unit; and f) carrying out steps a) to e) for a predetermined number of repetitions for carrying out a series of measurements of variables.

2. The method according to claim 1, which further comprises using sensors to determine an impedance of a sample situated in the measurement module at a predetermined number of frequencies.

3. The method according to claim 1, which further comprises:
   forming the measurement module as a passive measurement module; and
   performing the bidirectional transmission of the data to transmit measured variables and control pulses.

* * * * *